United States Patent [19]

Boyan et al.

[11] Patent Number: 5,492,697
[45] Date of Patent: Feb. 20, 1996

[54] BIODEGRADABLE IMPLANT FOR FRACTURE NONUNIONS

[75] Inventors: Barbara D. Boyan; Chandra M. Agrawal; James D. Heckman, all of San Antonio, Tex.

[73] Assignee: Board of Regents, Univ. of Texas System, Austin, Tex.

[21] Appl. No.: 403,513

[22] Filed: Mar. 13, 1995

Related U.S. Application Data

[60] Continuation-in-part of Ser. No. 162,633, Dec. 2, 1993, Pat. No. 5,397,572, which is a division of Ser. No. 528,968, May 24, 1990, abandoned, and a continuation of Ser. No. 914,992, Jul. 16, 1992, Pat. No. 5,290,494, which is a continuation of Ser. No. 528,968, May 24, 1990, abandoned, which is a continuation-in-part of Ser. No. 489,078, Mar. 5, 1990, abandoned.

[51] Int. Cl.⁶ .................................................. A61F 13/00
[52] U.S. Cl. ............................... 424/422; 424/426; 623/11
[58] Field of Search .................................. 424/422, 426; 623/11

[56] References Cited

U.S. PATENT DOCUMENTS

| 5,290,494 | 3/1994 | Coombes et al. | 264/41 |
| 5,397,572 | 3/1995 | Coombes et al. | 424/426 |

*Primary Examiner*—Morton Foelak
*Attorney, Agent, or Firm*—Greenlee and Winner

[57] ABSTRACT

A biodegradable implant for placement in nonunion bone fractures as a substitute for bone graft material is provided which is a flat plate or disk having a thickness of between about 1 mm and about 15% of the length of the bone, interconnected micropores, and canals substantially equivalent in size and spacing to naturally-occurring Haversian canals. The implant may additionally comprise additives such as growth factors, including bone morphogenic protein. In a preferred embodiment the implant is formed from a biodegradable polymer such as a polylactic acid-polyglycolic acid copolymer by a gel casting technique followed by solvent extraction to precipitate the implant as a microporous solid.

18 Claims, 5 Drawing Sheets

BIODEGRADABLE IMPLANT FOR FRACTURE NONUNIONS

CROSS REFERENCE TO RELATED APPLICATIONS

This application is a continuation-in-part of Ser. No. 08/162 633 filed Dec. 2, 1993, now U.S. Pat. No. 5,397,572, which is a divisional of Ser. No. 07/528,968 filed May 24, 1990, now abandoned, and a continuation of Ser. No. 07/914,992 filed Jul. 16, 1992, now U.S. Pat. No. 5,290,494, which is a continuation of Ser. No. 528,968 filed May 24, 1990, now abandoned, which is a continuation-in-part of Ser. No. 07/489,078 filed Mar. 5, 1990, now abandoned. All the foregoing patents and applications are incorporated by reference herein in their entirety.

FIELD OF THE INVENTION

This invention relates to biodegradable tissue implants to aid in healing of bone fracture nonunions.

BACKGROUND OF THE INVENTION

A fracture which fails to heal for a year and a half to three years is termed a fracture nonunion. It is characterized by pain, inability to bear weight and morbidity. Causes of fracture nonunions are thought to include too large a gap between the bone ends, micromotion present during the healing period, and/or lack of adequate vascularization.

Nonunion of long bone fractures is a serious complication of fracture healing, and usually results in long-term disability. Although nonunion develops in only one to five percent of all diaphyseal fractures, it is estimated that 100,000 nonunions of long bones occur in the United States annually (Calandruccio, R., ed. "Musculoskeletal system research: Current and future research needs," (ed 1981) American Academy of Orthopaedic Surgeons, Chicago). Failure of fracture healing results in pain, instability, and associated loss of function of the involved limb. In addition, because a significant number of fractures occur in young, productive individuals, the degree of disability produced by this problem is substantial.

During normal fracture healing, periosteal new bone is formed, and undifferentiated mesenchymal cells form fracture callus, proliferate, and differentiate into chondrocytes. These cells calcify their cartilaginous matrix, which then undergoes vascular invasion, resorption, and formation of bone on the scaffold of calcified cartilage. (Brand, R. A. and Rubin, C. T. (1990), "Fracture Healing," In Surgery of the Musculoskeletal System (C. McC. Evarts, Ed.) vol. 1 pp. 93–114, New York, Churchill Livingstone.) When there is a nonunion, however, periosteal new bone fails to bridge the defect, and the connective tissue that joins the fragments of bone develops into fibrocartilage. The matrix does not calcify, and osseous union and healing are not achieved. (Heckman, J. D., et al. (1991), "The Use of Bone Morphogenetic Protein in the Treatment of Non-Union in a Canine Model," J. Bone and Joint Surg. 73-A:750–764; Santos Neto, F. L. and Volpon, J. B. (1984), "Experimental Nonunion in Dogs," Clin Orthop. 187:260–271.)

The standard clinical approach at this time to achieving healing of nonunions involves a variety of surgical procedures designed to stabilize the nonunion and simultaneously stimulate new bone formation (Boyd, H. B., "Symposium: Treatment of ununited fractures of the long bones," J. Bone and Joint Surgery 1965 47A:167–168; Nicoll, E. A., "Fractures of the tibial shaft: survey of 705 cases, " J Bone and Joint Surgery 1964 46B:373–387). These treatment modalities generally incorporate the techniques of internal fixation combined with autogenous bone grafting and have a success rate varying from 85 to 95 percent (Edmonson, A. S. and Crenshaw, A. H., ed. Campbell's Operative Orthopaedics, (1987) 7th ed., CV Mosby, St. Louis). Iliac crest autograft has been shown to be an effective graft material (See, for example, Goldstrohm et al., J. Trauma, 24:50–58, 1984), but the supply is limited, requiring, in some cases of segmental defect repair, multiple procedures to obtain sufficient material.

Significant complications are associated with the harvest of autologous bone graft material (Younger, E. M. and Chapman, M. W., "Morbidity at bone graft donor sites," J. Orthopaedic Trauma (1989) 3:192–195). The removal of cancellous graft can create additional surgical trauma, increase the potential for infection, and, by lengthening the operating time, increase the risk. One alternative may be to use exogenous bone growth factors to stimulate bone growth at nonunion sites (Cornell, C. N. and Lane, J. M., "Newest factors in fracture healing," Clin Orthopaedic Relates Res. (1992) 227:297–311).

These disadvantages have spurred investigations of alternative bone repair materials. Bioceramics of calcium phosphate have attracted widespread attention because of their biocompatibility and chemical similarity to the bone matrix, which results in direct bonding to bone without intervening fibrous tissue (Osborn et al., *Biomaterials,* Winter, Gibbons, Plenk (eds.) 1980). However, they tend to be brittle, difficult to shape, and remain in the repair for time periods greater than 12 months (Holmes et al., *Clin. Orthop. Rel. Res.* (1984) 188:252–262).

Tricalcium phosphate disks have been used for treatment of craniotomy wounds in rabbits. (Hollinger, J. O., et al. (1989), "An evaluation of two configurations of tricalcium phosphate for treating craniotomies," J. Biomedical Materials Research 23:17–29.) Polylactic acid both with and without canine bone morphogenic protein was molded into the shape of nonunion defects created in dogs to create friable implants for evaluation. Modest healing was observed with the implant alone; bridging of the defect was observed with the implant containing the canine bone morphogenic protein. (Heckman, J. D., et al. (1991), "The Use of Bone Morphogenetic Protein in the Treatment of Non-Union in a Canine Model," J. Bone and Joint Surg 73A:750–764.)

Metal internal fracture fixation plates, produced for example from stainless steel, frequently have an elastic modulus greater than ten times that of bone. Although plate rigidity is an advantage for achieving primary osseous union, it tends to inhibit external callus formation, which is considered a good method for restoring the strength of the broken bone to its original level (Kelley et al., *Advances in Biomedical Polymers,* Gebelein, C. G. (ed.), Plenum Press, New York, 1987). Active remodeling of the bone after fracture healing may also be compromised unless the rigid plate is removed, often resulting in stress protection and, consequently, osteoporosis and atrophy beneath the plate.

The potential advantages of internal fixation devices produced from biodegradable polymers have long been recognized. Primary bony union and callus formation can be achieved by an adequately stiff and strong plate. Load transfer to the healing bone and bone remodeling may be promoted by a gradually reducing plate stiffness as biodegradation proceeds. Finally, the need for plate removal is eliminated by resorption of the device.

Kulkarni et al., *Arch. Surg.*, 93:839–43 (1966) describe the production of poly(DL-lactic acid) pins for reduction of mandibular fractures in dogs. Getter et al., *J. Oral Surg.*, 30:344–48 (1972), describe the use of high molecular weight PLA plates to treat mandibular fractures in dogs. Leenslag et al., *Biomaterials*, 8:70–73 (1987), disclose treatment of fractured zygoma in 10 patients using high molecular weight PLA plates. Such polymers, however, tend to be absorbed very slowly. Bostman et al., *J. Bone and Joint Surgery*, 69-B, No. 4 (1987), describe the use of high strength, fast resorbing, self-reinforced PLA/PGA rods for routine treatment of patients with displaced malleolar fractures.

The poly alpha-hydroxy acids are a class of synthetic aliphatic polyesters, the main polymers of which are polylactide (alternatively referred to as polylactic acid) and polyglycolide (alternatively referred to as polyglycolic acid). These materials have been investigated for use in a variety of implant systems for soft tissue and osseous repair in medicine and dentistry, since they tend to exhibit very good biocompatibility and are biodegradable in vivo. The need to remove the device after tissue repair can thereby be reduced or eliminated. The alpha-hydroxy acids are also being investigated for production of controlled release rate delivery systems for bioactive materials, such as pharmaceuticals.

The ability to vary the biodegradation rate of synthetic alpha-polyesters by material selection, copolymerization, control of molecular weight, crystallinity and morphology makes them attractive for bone repair. Resorption rate can be varied from two weeks to over a year, for example, so that implant resorption may be tuned to bone repair rates (Hollinger et al., *Clin. Orthop. Rel. Res.*, 207:290–305, 1986) PLA/PGA copolymers have been used alone (Hollinger, *J. Biomed. Mater. Res.*, 17:71–82, 1983) and as binders for bioceramics (Haggish et al., *Biomaterials*, 7:183–87, 1986) and decalcified allogeneic bone (Schmitz et al., *Clin. Orthop. Rel. Res.*, 237:245–55, 1988) to produce bone fillers for repairing bony deficiencies in animals.

Such polymers can also function as delivery systems for growth factor(s) as they biodegrade. U.S. Pat. No. 4,578,384 discloses a protein-acidic phospholipid addition to PLA/PGA copolymer which is reported to increase bone healing rates in rat tibias relative to the copolymer. PLA could, in itself, play a dual role of bone filler and bone growth factor. Hollinger, *J. Biomed. Mater. Res.*, 17:71–82 (1983), reported that a 50:50 copolymer of poly(L-lactic co-glycolide) increased the rate of early osseous healing when implanted in rat tibial defects. Thus, it appears that the degradation characteristics of these linear aliphatic polyesters may play a role in the stimulation of hard and soft tissue growth, which increases the attraction of using PLA and PGA for repairing soft or hard tissue.

The lactide/glycolide polymers and copolymers tend to demonstrate an easily characterized and controllable degradation rate and tend to be nontoxic, which is advantageous for manufacture of controlled release rate delivery systems for a wide variety of bioactive materials, such as pharmaceuticals. U.S. Pat. No. 4,563,489 discloses production of a biodegradable polymer delivery system for bone morphogenetic protein based on a poly(lactide co-glycolide) copolymer. Development of suitable delivery methods is important for such therapeutic proteins since they are readily absorbed by the body. Schakenraad et al., *Biomaterials*, 9:116–20 (1988), describe the development of a biodegradable hollow fiber of poly(L-lactide) for controlled release of contraceptive hormone.

U.S. Pat. No. 4,719,245, and related U.S. Pat. No. 4,800,219 disclose compositions wherein segments of poly(R-lactide) interlock or interact with segments of poly(S-lactide), producing a crystalline phase having a melting point higher than that of either component. Processes are described for preparing the above compositions, e.g., by mixing and combining the previously prepared polymeric components in a suitable solvent or in the molten state and processes for preparing gels and porous structures of the compositions. The patent discloses spontaneous gel formation from solutions of blended polylactide enantiomers on stirring. It is described that porous structures are produced from gels of the composition by a process comprising solvent exchange and evaporation.

U.S. Pat. No. 4,883,666 describes discs 3 mm in diameter made by solvent casting of ethylene vinyl acetate slabs containing dopamine coated with ethylene vinyl acetate for linear release of L-dopa for treatment of disorders of the nervous system. The reference states that polylactic acid and polyglycolic acid can be used as carriers, however, methods for achieving the required linear release are not disclosed. U.S. Pat. No. 5,330,768 describes the use of block copolymers of polyethylene oxide and polypropylene oxide in polylactic acid and polyglycolic acid polymer formulations for control of drug release rate. This patent discloses that fast release of an initial burst of additive may be controlled by slow removal of organic solvent from the polymer at low temperatures and by adding the block copolymer. No initial burst of drug release is reported in U.S. Pat. No. 5,336,505 which employs bioerodible ortho ester polymers for implants and other pharmaceutical preparations.

U.S. Pat. No. 4,637,931 discloses production of a bone repair material consisting of decalcified freeze-dried bone (DFDB) and biodegradable biocompatible copolymer, namely poly[L(–) lactide co-glycolide] copolymer, which is described as being used for improving and accelerating the healing of osseous tissue.

U.S. Pat. No. 4,578,384 discloses a material, consisting of a combination of a proteolipid and a biodegradable, biocompatible copolymer which is stated to facilitate improved healing of osseous wounds when implanted at the site of the broken tissue.

The methods disclosed in U.S. Pat. Nos. 4,637,931 and 4,578,384 for producing biodegradable bone repair materials from polymer solutions generally comprise the stages of polymer dissolution, polymer precipitation in a nonsolvent, partial drying of the precipitate and compaction of wet precipitate in a mold, followed by heating/drying to produce the finished implant.

U.S. Pat. No. 4,563,489 discloses a biodegradable PLA polymer delivery system for bone morphogenetic protein (BMP) to induce formation of new bone in viable tissue. The delivery composition described is substantially pure BMP in combination with a biodegradable PLA polymer, prepared by admixing the BMP with the biodegradable polymer. The composition is implanted in viable tissue where the BMP is slowly released and induces formation of new bone.

The method for preparing the implant material of U.S. Pat. No. 4,563,489 generally comprises (1) dissolving the physiologically acceptable biodegradable polymer in a solvent such as ethanol, acetone or chloroform, (2) admixing the polymer solution with BMP to form a dispersion of BMP in the polymer solution, and (3) precipitating the composite by adding a second solvent which causes precipitation of the polymer or lyophilizing the dispersion or otherwise treating the dispersion to remove it from solvent and form the BMP-PLA composite. After composite formation, it is filtered, pressed or otherwise processed to remove the solvent, and the resulting composite solid is formed into the desired shape for implantation. Other additives may be included, e.g., antibiotics, prosthesis devices, radio-opacifying agents.

The delivery compositions of U.S. Pat. No. 4,563,489 have relatively small masses and are used in relatively thin layers (i.e., in the range of 1 mm to 2 mm in thickness). In one example, implants are described as being shaped by pressing the wet BMP-PLA precipitate in a mold to express the second solvent prior to drying. Wet (precipitated) composite was also shaped using glass molds to produce flakes, rods, films or plates. The patent also mentions that in preferred embodiments the BMP/biodegradable polymer delivery composition is formed into a dough, rod, film, flake or otherwise shaped as desired. The patent further mentions that the BMP/PLA composition, while still dispersed or dissolved in solvent, may be formed into small pellets, flakes, platelets, etc., by casting in molds and allowed to dry or harden.

U.S. Pat. No. 4,645,503 discloses production of a moldable bone implant material containing approximately 65–95% hard filler particles and a binder composed of approximately 35–50% of a biocompatible, biodegradable thermoplastic polymer which has fluidic flow properties at a selected temperature at or below about 60° C. Variation in biodegradation rate via the usual routes for biodegradable polymers is described, namely (1) adjustment of molecular weight, (2) substitution of the polymer subunit (copolymerization), (3) blending with a slower degrading polymer, or (4) increasing the surface area for hydrolysis by varying the proportion of binder and particles to provide voids or pores in the material.

All publications and patents referred to herein are hereby incorporated by reference in their entirety.

SUMMARY OF THE INVENTION

Figure 1:
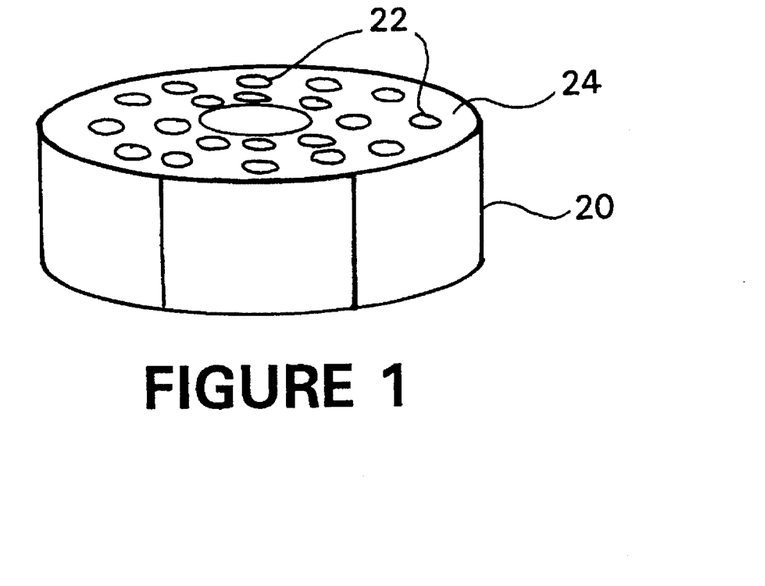
FIG. 1 is a perspective view of an implant made of a resorbable material provided by this invention.
Figure 2:
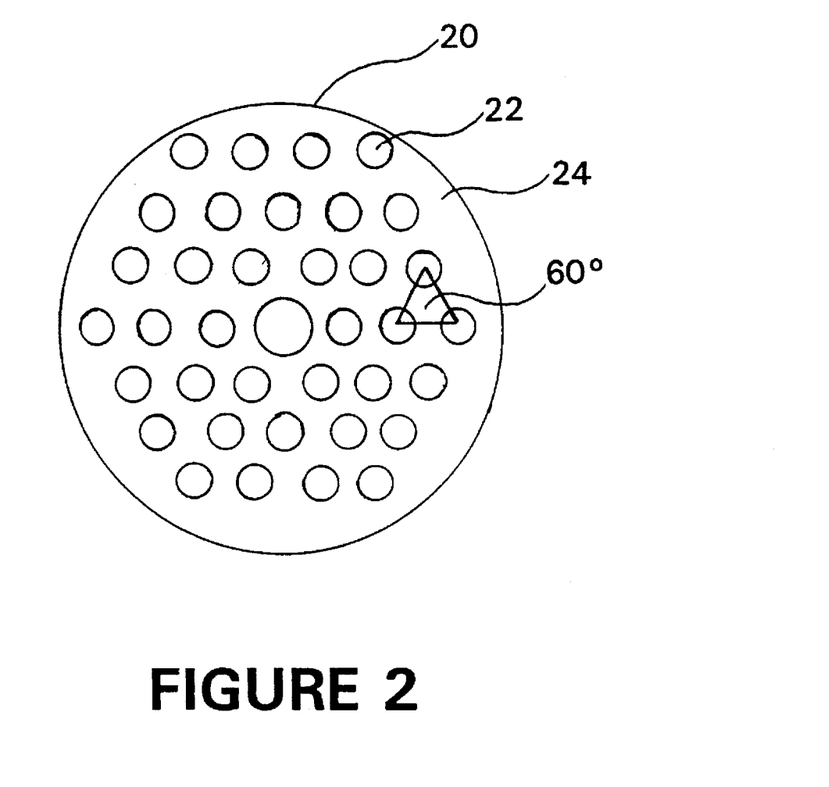
FIG. 2 is a plan view of the implant of FIG. 1.

An implant having a honeycomb structure for placement in nonunion bone fractures is provided as a bone graft substitute comprising:

a. interconnected pores having an average diameter of between about 5 μm and about 20 μm constituting a void volume of between about 40 and about 85 percent of said implant, and preferably between about 60 and about 85 percent of said implant;

b. canals having a size, shape and spacing substantially corresponding to naturally-occurring Haversian canals;

c. having a thickness of between about 1 mm and up to about 10% to 15% of the length of the bone;

d. having a perimeter shaped to substantially correspond to the cross-section of the ends of said non-union bone fracture, typically having a circular perimeter with a diameter corresponding to that of the bone in which it is to be placed, e.g. about 10 to about 40 mm; and e. having a carvable, non-friable consistency. Haversian canals are canals naturally occurring in cortical bone which allow vascularization therethrough. They are found at the center of osteons which vary in size, being made up of 15 to 20 lamellae of cells, each lamella being 3–7 μm thick (Textbook of Histology, Bloom and Fawcett, 1980). Haversian canals are between about 150 and about 250 μm from each other and have a diameter between about 10 μm and about 100 μm. The canals are about 3 to about 5 mm in length and vary in shape from round to oval. The implants of this invention have canals preferably having a diameter of between about 0.1 and about 1.0 mm and spaced at least about 1 mm apart, placed concentrically about a larger central channel, which preferably has a diameter corresponding to the medullary canal of the bone in which the implant is to be placed, e.g., about 7 to about 35 mm in diameter. Preferably these canals (also called macropores or macroporous channels herein) are placed as shown in FIGS. 1 and 2; however macroporous channels may also or alternatively be placed at right angles to those shown in the Figures. The implants of this invention are suitable for placement in any type of nonunion fractures including fractures in the following types of bones: long bones such as the bones of the arms and legs, the mandibles, cranium, pelvis, phylanges, ribs, cranium, spine, etc. These implants are useful for stimulation of bone healing to bridge the nonunion defect in such types of bones regardless of whether the bones contain naturally-occurring Haversian canals. Growth of cortical bone having Haversian canals, as well as the bone trabeculae and bone marrow, are stimulated.

Good healing of nonunion defects of up to about 3 times the diameter of the treated bone and preferably between about 3 and about 5 mm in width is achieved with the use of the implants of this invention. The implant of this invention is preferably in the shape of a flat plate sized to fit the thickness of the defect, preferably about 2 to about 5 mm in thickness. The perimeter of the plate is preferably the shape of the cross section of the nonunion defect, typically circular as in the case of long bones. Circular discs can also be used in the case of mandibular bones and the cranium. The implant may be cast into the proper shape, or may be cast as a roughly or substantially circular shape, then carved or milled to conform to the shape of the defect into which it is to be placed. Typically, the perimeter of the implant is between about 8 mm for small bones such as the finger, up to about 6–8 cm for large bones such as the femur.

The implant need not be of weight-bearing strength, but should be nonfriable such that it does not crumble upon carving or milling.

The implants of this invention are preferably composed of a bioerodible polymeric material, and formed by gel casting. Many such polymeric materials are known to the art. Preferably, the implant is made of resorbable synthetic alpha-polyester, such as polylactic acid polymers, polyglycolic acid polymers or copolymers or blends thereof. A preferred polymeric material is a polylactic acid polymer or a 50:50 polylactic acid-polyglycolic acid copolymer. The polylactic acid polymer may be an enantiomeric polymer (D-PLA or L-PLA), or may be a racemic mixture of both enantiomers. Preferably the average molecular weight of the polymer is between about 45,000 and 200,000.

In order to alter the resorption rate or other characteristics of the product, a second material (e.g. another polymer) may be dissolved in the solvent before the gel forming step. To obtain satisfactory gelling, the ratio of the first polymeric material to the second material should be at least about 1:9, with the addition preferably being made to a solution having a concentration of at least about 2.5% (w/v) of the first polymeric material. Depending upon the desired properties of the final product, the second material can be selected from numerous possibilities, such as lactides, polymers of alpha-hydroxy acids, polymers of lactones, copolymers of at least one alpha-hydroxy acid, polyethylene oxides, polyurethane or copolymers containing a thermoplastic elastomer, e.g. polyether or polyester. Alternatively, or in addition, a filler material may be added to the solvent before the gel forming step.

The implant of this invention preferably comprises a central channel therethrough of a size corresponding to the central canal of the bone in which it is to be placed; preferably, this central channel has a diameter of between about 7 mm and about 35 mm.

Good healing occurs through the use of implants of this invention in the absence of additives such as growth factors; however, in one embodiment, the implant comprises an additive selected from the group consisting of therapeutically active substances, degradation enhancers, and degradation retardants. Therapeutically active substances include antibiotics, immune modulators, lymphokines, monokines, cytokines, enzymes, antibodies, growth promotants, growth inhibitory factors, blood proteins, hormones, vaccines, blood coagulation factors, medicaments including pain medications, and therapeutically active substances such as bioactive ceramics, inorganic salts, hydroxyapatite and others known to the art.

A preferred class of additives include growth factors such bone morphogenic protein (BMP), transforming growth factor beta and platelet derived growth factor, osteogenic growth factors such as bone-derived growth factor, activin, insulin-like growth factor, basic fibroblast growth factor and combinations thereof.

Degradation enhancers and retardants are known to the art. It has been discovered by applicants herein that surprisingly, incorporation of a protein, preferably having a molecular weight greater than or equal to about 15,000, retards degradation of the polymer. Thus a preferred degradation agent of this invention comprises a protein, e.g. collagen, bone morphogenetic protein, transforming growth factor beta, serum albumin, or alkaline phosphatase. The protein should be nonimmunogenic, e.g. human protein should be used in humans, dog protein in dogs, etc.

The implants of this invention are preferably produced by a polymer gel casting method. Such methods are known to the art, for example as described in U.S. Pat. No. 4,962,091. The biodegradable polymer is dissolved in a solvent, preferably acetone or ethyl acetate, and more preferably acetone, and allowed to gel in a mold. The gel is then dried to form the resorbable material product, or preferably, after the gel is formed, the solvent is replaced/extracted with a nonsolvent such that the polymer precipitates to form a substantially microporous material. The microporous material is then dried to form the product. The gel may be partially dried followed by extraction of the organic solvent, then complete drying.

The process preferably comprises:
  a. solubilizing said polymer in a suitable solvent such as acetone or ethyl acetate to form a solution;
  b. allowing said solution to gel in a mold to form said implant;
  c. removing said gel from said mold;
  d. removing said acetone from said gel.

The acetone is preferably removed from said gel by means of solvent extraction such as with water, or an organic liquid such as methanol or ethanol. More consistent results are obtained using the alcohols. In a most preferred embodiment, the acetone is extracted/replaced successively with 1:2 methanol:acetone, 1:1 methanol:acetone, and 2:1 methanol:acetone solutions. Ethanol may be used instead of, or in addition to, methanol.

The additives to be incorporated into the implant are preferably added to the original polymer solution prior to gelling at a concentration of between about 1 ng/ml and about 2 mg/ml. In some formulations an excess of up to about 1,000 percent is required in order to ensure an implant having the desired additive concentration. Preferably the additive is present in the implant at a concentration of between about 0.1 ng/ml and about 200 ng/ml.

More preferably the process for making the implants of this invention comprises:
  a. solubilizing a biodegradable polymer precursor in a suitable solvent such as acetone or ethyl acetate to form a solution;
  b. allowing said solution to gel in a mold comprising tines, e.g. of piano wire, spaced to form canals in said implant having a size, shape and spacing substantially corresponding to Haversian canals;
  c. removing said gel from said mold;
  d. removing said acetone from said gel by solvent extraction whereby said polymer precipitates as a microporous solid having pores about 5 to about 20 μm and forming a void volume between about 40 and about 85%, and preferably between about 60 and about 85% of said implant.

When the additive is a protein having a molecular weight of more than about 15,000 and/or the protein has a tendency to aggregate, the process also preferably comprises rotating said mold during step b. at a speed of at least about one-fourth revolution per minute to about one-half revolution per minute whereby said protein remains evenly distributed throughout said solution during gel formation.

The implants of this invention preferably release between about half and about two-thirds of the additive within the first two days of implantation in vivo, and thereafter continuously release a substantially constant amount of the additive over the degradation period of said implant. Typically the daily release rate of the additive in vitro subsequent to the first two days is between about 0.03 and about 1.5% of the total incorporated.

Implants of this invention may also be made by a process as disclosed in U.S. Ser. No. 08/123,812, incorporated herein by reference, utilizing a mold of the appropriate size and shape.

This invention also provides a method for treating a nonunion bone fracture comprising placing into said fracture the implants of this invention as described above.

In chronic nonunion fracture pathologies, the defect may be filled with nonbony tissue. The usual treatment is to perform surgery to remove the nonunion tissue, and place the ends together, keeping them in place by means of metal plates placed across the sides of the fracture. To avoid shortening of the bone, the space-filling implant of this invention is placed in the defect. As the defect heals, the implant is degraded and replaced by osseous tissue and need not be removed. It is not usually necessary to remove the metal plates.

DETAILED DESCRIPTION OF THE PREFERRED EMBODIMENTS

One preferred embodiment of the invention relates to a gel casting technique for resorbable synthetic alpha-polyesters, which may be used for producing novel bone repair materials or bone substitutes, resorbable medical implants and timed release carriers for medication. Formation of a distinct gel phase in the techniques of this invention enables production of relatively thick-section, solid moldings.

The gel may be used as a medium to incorporate non-gelling or weakly gelling polymers (such as low molecular weight species, non-lactide polymers, or lactide copolymers), in the material composition for control of properties such as resorption rate and density, mechanical properties, shrinkage, and thermal characteristics. Gel casting can be used to vary morphology (e.g. solid versus microporous materials) and to produce blends of homopolymers, copolymers and particulate fillers, such as tricalcium phosphate. Control of material biodegradation rate by variation of polymer type, molecular weight range, crystallinity and morphology may therefore be facilitated.

Other embodiments of the invention include processes for preparing gels from the gelling polymer and from blends of such polymer with resorbable and nonresorbable homopolymers, copolymers, and filler materials; processes for obtaining thick-section solid and microporous materials/foams from the gels, methods for controlling the shrinkage of microporous materials containing a substantial amorphous component by controlled drying and extraction of plasticizing molecules; and resorbable implants in the form of honeycomb structures for repair of long bones, being manufactured from microporous gel cast materials.

In a preferred embodiment, the gelling medium is a PLA-PGA copolymer having an average molecular weight of around 45,000 daltons which is sold commercially by Medisorb, Inc. of Cincinnati, Ohio.

The solvent may be acetone or ethyl acetate. Acetone is preferred since polymer dissolution is generally easier in this solvent.

Dissolution of a potential gel-forming polylactide polymer in acetone appears to be highly dependent on the physical form of the starting material. A decrease in crystallinity of the starting polylactide will also facilitate its dissolution in acetone and increase its potential for use as a gel-forming medium.

Useful polymers and copolymers for blending with the gelling medium include lactide homopolymers, non-lactide polymers such as poly epsilon carpolactone, lactide copolymers, copolymers produced from mixtures of lactide and non-lactide comonomers such as lactones (e.g. epsilon caprolactone) or other hydroxy acids (e.g. glycolic acid), lactides, non-lactide polymers (e.g. polyethylene oxide), or copolymers containing "soft blocks" of polyether, polyester or other similar polymers. Such blending may enable variation of molecular weight distribution, density, shrinkage, and mechanical and thermal characteristics.

Useful fillers include particulates of bioceramics such as tricalcium phosphate and hydroxyapatite; non-resorbable discontinuous fibers of alumina, carbon or polyethylene terephthalate; or resorbable discontinuous fibers such as polyglycolic acid or calcium metaphosphate.

In a preferred embodiment of this invention, a method is provided for preparing solid resorbable materials, comprising the steps of:

(1) polymer dissolution in a solvent;

(2) casting the solution in a mold;

(3) gel formation in situ;

(4) removal of the shaped gel from the mold; and (5) drying to obtain solid material in relatively thick sections.

Solid materials may alternatively be produced by extracting the solvent with a nonsolvent (e.g. methanol) over around 24 hours before drying, then drying the material. Shrinkage may result in material consolidation to form a solid core encased in a layer of microporous material. This latter material may be removed by machining if desired.

For highly crystalline polymers, e.g. polylactide, the gel casting method described above may be altered to produce microporous materials (or foams) of good structural integrity and foam consistency by following the steps (1)–(4) above, then converting the gel to a microporous material by precipitation in a nonsolvent such as methanol, followed by drying.

The density of microporous blends containing certain amorphous polymers can be controlled by predrying and water immersion subsequent to gel production. Extraction of solvent may remove the plasticizing effect of organic molecules, thereby restricting chain recoiling of the amorphous phase, which may result in material shrinkage on drying.

If substantially amorphous polymers or semi-crystalline polymers are included with the basic gelling polymer, the product gel may be converted to a microporous material by precipitation in an organic nonsolvent, and/or immersion in water to remove the plasticizing effect of organic molecules, followed by drying. Also, the extent of shrinkage and, therefore, density of microporous materials containing a substantial proportion (e.g. about 25%) of amorphous polymer can be controlled by partially drying the gel (or the methanol-treated gel) to a desired level and extracting/replacing the solvent or nonsolvent with water prior to drying. This may remove the plasticizing effect of the organic solvent or nonsolvent molecules, which may facilitate chain recoiling in the amorphous phase, resulting in excessive shrinkage of the material on drying.

The resorption rate of biodegradable polymers may be influenced by the material form. Porosity generally facilitates fluid ingress throughout the material, exposing a large surface area of the material to chain scission by hydrolysis. Increased degradation rates can be expected. Porous implant surfaces present a favorable surface for cell attachment and growth, enhancing the implant's function as a biodegradable scaffold for tissue repair or implant fixation.

The release rate of medication from resorbable, polymeric delivery systems may also be influenced by the porous character and density of the delivery vehicle. The control of density and, therefore, pore size and structure in resorbable polymers may be achieved by the above-described drying/water treatment stage in the process of manufacture of microporous materials from blends containing an amorphous polymeric component.

The resulting solid or microporous materials can be used to form implantable devices of various shapes, preferably discs for nonunion fractures. Advantages of a microporous material include the increase in surface area for hydrolysis or breakdown of the implant and the presence of a potentially better surface for attachment of osteoprogenitor cells.

As illustrated in FIGS. 1 and 2, the material can be machined to produce a bone graft substitute 20 of macroporous character, for example by drilling 100–500 µm bores 22 running the length of the implant and intersecting with the implant end surfaces 24. In one embodiment, the macropores are about 500 µm in diameter. The center hole is about 2 mm in diameter, and the macropores are spaced about 1 mm from each other, center to center. In repair of long bones, the macropores allow migration throughout the implant to establish a supply of osteoprogenitor cells and growth factor and allow primary bone growth and vascularization along the pore channels. Gradual resorption of the implant bridge allows secondary bone formations to be established and bone remodeling to take place by load transfer to the ingrown tissue. A polymer blend of slow-resorbing polymer (L-PLA) and fast-resorbing polymer [e.g. poly(DL-lactide co-glycolide)] can be used to produce an "enduring scaffold" system which provides a support element for immature bone formations during and after resorption of the fast-degrading phase to promote and encourage satisfactory tissue repair, stability and remodeling.

In another embodiment of this invention the material used is a 50:50 copolymer (PLG50) of PLA and PGA having an intrinsic viscosity of 0.65 dL/g and a molecular weight of 45,000 daltons, of Medisorb Inc., Cincinnati, Ohio.

A circular implant having a thickness of about 2.5 mm and a diameter of about 13.5 mm is formed, as shown in FIGS. 1 and 2, is formed by gel casting. The polymer is solubilized in acetone, placed in a mold and allowed to stand until a gel is formed. The acetone is extracted by immersing in mixtures of methanol and acetone having successively higher concentrations of methanol. The implant precipitates as a microporous solid with pores approximately 5 to 20 µm in size.

In another embodiment, a therapeutically active additive is added to the acetone/polymer solution prior to gel formation. The additive is released in an initial burst which augments initial wound healing, followed by a second, essentially continuous and steady release which fosters differentiation and maturation of the cells to form bone tissue bridging the nonunion.

When such an additive is used, the mold is preferably rotated at a rate of about one-fourth to one-half revolution per minute to keep the additive evenly distributed throughout the material and prevent settling while the gel is forming.

EXAMPLES

The following examples are designed to illustrate certain aspects of the present invention. The examples are not intended to be comprehensive of all features and all embodiments of the present invention, and should not be construed as limiting the claims presented herein.

Material shrinkage was measured with respect to the diameter of the gel on demold. Material density was estimated from measurements of the dimensions of a disc of material and its corresponding weight in air. Drying of materials was carried out in air under ambient conditions unless otherwise specified. Polymer dissolution was aided by stirring with a magnetic stirrer bar and, unless otherwise specified, the mold was a 10 cc plastic syringe body.

EXAMPLE 1

A single component gel was produced by heating finely divided L-PLA (Polysciences, Inc., MW 100,000, Batch No. 61490) in acetone at a concentration of 7–9% (w/v), with agitation at a temperature of 46°–52° C., until dissolved (approximately 15 minutes). 7% (w/v) gave the best results.

The clear solution was poured into a mold and allowed to cool to room temperature under quiescent conditions. The cloud point, or the point at which opacity developed in solution due to crystal formation, was accompanied by a marked increase in solution viscosity, and occurred at approximately 28°–32° C. for a 10% (w/v) solution. A weak gel was formed at 25° C., which was easily disrupted by stirring. The product gel which formed in situ in the mold had a distinct white color and hardened over time. It was firm enough to withstand demold after 30 minutes at room temperature (22°–24° C.). At that point, the demolded gel was allowed to dry to remove the solvent and produce solid material. A shrinkage in diameter of approximately 50% relative to the demolded gel occurred after 24 hours air drying.

EXAMPLE 2

A demolded gel prepared as in Example 1 was immersed in methanol to extract solvent and produce a microporous material on subsequent drying.

An acetone-based gel produced from a 7% (w/v) solution was immersed in methanol for three days (50 cc methanol in 100 cc beaker with a change of immersion medium at 24 hours). The methanol was allowed to evaporate and the material allowed to dry in the beaker over four days at room temperature. A shrinkage of approximately 40% occurred relative to the gel on demold and a density of 0.35 gm/cm³ was obtained for the product foam/microporous material. Treatment of the demolded gel in methanol for three days, followed by water immersion for three days, with a change in immersion medium after 24 hours, slightly reduced the shrinkage to 37% and yielded a microporous material density of 0.33 gm/cm³ after drying for four days at room temperature.

An acetone-based gel of the preferred L-PLA polymer produced from a 7% (w/v) solution was redissolved by heating in an excess of solvent (e.g. 1.1 gm gel in 10 cc acetone) at 50° C. in less than ten minutes.

EXAMPLE 3

A 2.5% (w/v) solution of L-PLA (MW 100,000) in acetone was produced by dissolving 0.5 gm of the polymer in 20 cc of solvent at 50° C. The solution was poured into molds. On standing at room temperature, opacity developed in solution after 45 minutes, denoting crystal formation. On demold after 19 hours, a strong, white gel was evident, which exhibited a 65% shrinkage in diameter after five hours air drying at room temperature.

EXAMPLE 4

L-PLA of molecular weight 200,000 (Polysciences, Inc.), when heated in acetone at 50° C. at a concentration of 2 gm polymer to 20 cc of solvent, did not dissolve completely. Instead, a milky suspension of powder in solvent was obtained. A weak gel was, however, formed from this suspension after one hour at room temperature, presumably due to dissolution of a certain fraction of the starting polymer. This same polymer dissolved readily in p-dioxane to give a 10% (w/v) solution, but did not gel under quiescent conditions at room temperature. L-PLA, with a weight average molecular weight of 50,000 (Polysciences, Inc.) when heated in acetone at a 9% (w/v) concentration also resulted in incomplete dissolution (milkiness persisted). After standing at room temperature for 17 hours, a very weak, easily damaged gel was evident on demold which collapsed under its own weight. Doubling the concentration of 50,000 L-PLA in acetone also produced a weak gel on standing which cracked or crumbled on drying.

EXAMPLE 5

L-PLA, MW 100,000, exhibited a crystalline melting point at approximately 160° C. Rapid cooling in the molten state from 230° C. resulted in increasing amorphous content, evidenced by the absence of a recrystallizing transition on cooling. On reheating, no recrystallization of the amorphous component occurred.

In contrast, a weakly gelling lactide polymer (MW 50,000), which was substantially unsuitable for use, exhibited a recrystallizing transition at around 125° C., followed by a crystalline melting transition at 170° C. on reheating the amorphous form produced by rapid cooling. This reflected a greater chain mobility for this polymer.

These tests suggest that operable semi-crystalline polymers suitable for producing the gelling medium in the disclosed gel casting technique may be characterized by a limited chain mobility due to molecular weight distribution, which impedes recrystallization of the amorphous form of the polymer on heating.

EXAMPLE 6

Formation of a distinct gel phase immediately following polymer dissolution tends to enable production of thick solid moldings.

An 11 mm diameter cylinder of the 100,000 MW L-PLA was produced by air drying for 17 hours a gel produced from a 9% (w/v) solution in acetone, followed by annealing for 56 hours at 72° C. Final shrinkage (based on diameter) was 62%. In contrast, the absence of gelation in a 7% (w/v) solution of the preferred L-PLA polymer in chloroform at room temperature resulted in the formation of a film or coating on the mold walls on solvent evaporation over four days.

Shrinkage forces developed during drying of the gel at room temperature, yielding a homogenous, thick-section solid product with a state of consolidation visually similar to that of a thermoplastic processed in the melt at high temperatures and pressures by injection molding or extrusion. Material consolidation in gel casting was achieved in a "cold" system through a combination of factors. The gel's liquid medium provided crystal mobility and chain flexibility in the amorphous phase by a plasticizing effect. This, coupled with the forces generated by the tendency of macromolecules in the solvent-swollen, amorphous phase to recoil on evaporation of the swelling medium, resulted in the observed good material consistency.

EXAMPLE 7

An 11% (w/v) solution of low molecular weight L-PLA (MW 2000, Polysciences, Inc.) was produced by dissolving 2.2 gm polymer in 20 cc acetone at 52° C. and allowed to stand at room temperature for 21 hours. An extremely weak gel was evident on demold, which did not retain the molded form but collapsed under its own weight, eventually drying to a weak, brittle solid.

12% (w/v) solutions in acetone of poly(DL-lactic acid) (MW 20,000, Polysciences, Inc.) or 70:30 poly(DL-lactide co-glycolide) copolymer (MW 30,000–60,000, Polysciences, Inc.) or 90:10 poly(DL-lactide co-glycolide) copolymer (MW 30,000–60,000, Polysciences, Inc.) or 85:15 poly(DL-lactide co-glycolide) copolymer (MW 40,000–100,000, Dupont) did not gel on standing at room temperature. Gradual evaporation of solvent occurred from the bulk solution resulting in formation of a viscous fluid.

These polymers were combined with the preferred gelling L-PLA polymer, for example, in the ratio 25 (L-PLA):75 (other), by simultaneous dissolution in acetone to produce a blended polymer gel. The gel was subsequently converted to a solid material by drying/solvent extraction. For predominantly crystalline polymer additions, e.g. lower molecular weight L-PLA, the gel was converted to a microporous material by precipitation in a nonsolvent, followed by drying. For substantially amorphous polymer additions to the basic gelling polymer, the gel was converted to a microporous material by precipitation in a nonsolvent and/or immersion in water (to remove the plasticizing effect of organic molecules), followed by drying. Non-gelling or weakly gelling polymers were incorporated into a particular material composition by using L-PLA as the gelling medium.

EXAMPLE 8

A 30% solid, particulate-filled, resorbable material consisting of tricalcium phosphate in L-PLA was produced by dissolving 1.4 gm L-PLA (MW 100,000) in 20 cc acetone at 52° C. On dissolution of the polymer (in approximately 15 minutes), 0.6 gm of tricalcium phosphate (TCP) (J. T. Baker) was added, with stirring until a uniform dispersion was obtained. The suspension was poured into a mold and allowed to stand at room temperature. A strong, firm gel was obtained on demold after 1½ hours, which exhibited a shrinkage value of 55% over 29 hours air drying to yield a solid, particulate-filled material having a density of 1.02 gm/cm$^3$.

An acetone-based gel of TCP-filled L-PLA, produced as described above, was immersed in methanol on demold for five days, then air dried for four days. The microporous material obtained exhibited a shrinkage of 26% and a density of 0.27 gm/cm$^3$.

EXAMPLE 9

A 29% TCP particulate-filled microporous blend of L-PLA with 70:30 poly(DL-lactide co-glycolide) copolymer (MW 30,000–60,000, Polysciences, Inc.) was produced by dissolving 0.8 gm and 2.4 gm of each polymer, respectively, in 20 cc acetone at 52° C. Particulate filler (1.28 gm) was dispersed in the solution by stirring. The suspension was transferred to molds and allowed to stand at room temperature for 22 hours before demold, whereupon a weak, sticky gel was obtained. (Sedimentation of TCP filler was limited prior to gel formation by the viscosity of the blended polymer solution.) The gel was subsequently immersed in 50 cc methanol in a 100 cc beaker for two days with a solvent change at 24 hours. The nonsolvent was then allowed to evaporate and the material allowed to dry in the beaker over three days. The TCP particulate-filled L-PLA:PLG microporous blend obtained exhibited a shrinkage of 28% and a density of 0.6 gm/cm$^3$.

EXAMPLE 10

Solid L-PLA material (MW 100,000, Polysciences, Inc.) was produced by dissolving 1.8 gm of this gelling polymer in 20 cc acetone at 52° C. The solution was transferred to cylindrical molds and allowed to stand at room temperature. The gel obtained on demold after 39 minutes was air dried under ambient conditions to consolidate the polymer as a solid rod. Thermal transitions were determined by Differential Scanning Calorimetry (DSC). On heating at 20° C./min., from 10° C. to 230° C. a single melting peak was observed at 159° C. No recrystallization peak was evident on immediate cooling of the sample at 50° C./min. to 10° C. Reheating the sample at 50° C./min to 230° C. revealed only a glass transition (Tg) at 70° C., indicating that the polymer exists mainly in the amorphous phase after rapid cooling from the melt.

EXAMPLE 11

A 50:50 blend of L-PLA (MW 100,000) and poly(DL-lactide) (MW 20,000, Polysciences, Inc.) was produced by codissolving 1 gm of each polymer in 20 cc acetone at 52° C. The solution was poured into cylindrical plastic molds and allowed to stand at room temperature. The product blended gel was demolded after 55 minutes and air dried to consolidate the material as a solid rod. Thermal transitions were revealed by DSC, using the test procedure described in Example 10. A broad, spiky melting peak was observed on heating, extending from 120°–160° C. and centered around 140° C. No recrystallization peak was evident on cooling the sample. A glass transition was observed on remelting at 53° C.

The (DL-lactide) polymer showed a glass transition at 35° C. on heating, which shifted to 45° C. after cooling from 230° C. and reheating.

EXAMPLE 12

A 25:75 blended solution of high molecular weight L-PLA (MW 100,000) and low molecular weight L-PLA (MW 2,000, Polysciences, Inc.) was produced by dissolving 0.6 gm and 1.8 gm of each polymer, respectively, in 20 cc acetone at 50° C. The solution was transferred to molds and allowed to stand at room temperature. The resultant firm gel was demolded in 30 minutes, following a rapid cloud point of five minutes. Air drying the gel over five days resulted in a shrinkage of 44% and production of a hard, waxy solid. A 25:75 blended gel of high and low molecular weight L-PLA, demolded after 19 hours, was immersed in 50 cc methanol in a 100 cc beaker for two days with a change of medium after 24 hours. The methanol was allowed to evaporate and the material allowed to dry in the beaker over four days at room temperature. The blended, microporous material obtained exhibited a shrinkage of 19% and a density of 0.29 to 0.43 gm/cm$^3$.

The thermal testing procedure described in Example 10 revealed melting peaks at 136° C. and 155° C. for 25:75 microporous material, roughly corresponding to the individual homopolymer components, and no recrystallizing transition on cooling. On reheating, a glass transition was observed at 63° C., a broad recrystallizing transition at 130° C. and a melting peak at 155° C. Solid, low molecular weight L-PLA obtained by air drying the weak gel produced from an 11% (w/v) solution in acetone revealed low broad melting peaks centered around 104° C. and 118° C. and the main melting peak at 140° C. No recrystallization transition was observed on cooling. On reheating, a glass transition was evident at 50° C. and a small melting peak at 143° C.

The lower molecular weight polymer species introduced into the blend allowed sufficient chain mobility for recrystallization to occur from the amorphous form on heating. Recrystallization did not occur for the amorphous form of the single higher molecular weight polymer.

It may be possible to vary the crystallinity of a blend by isothermal conditioning.

EXAMPLE 13

A 25:75 blended solution of L-PLA and a 70:30 poly(DL-lactide co-glycolide) copolymer (MW 30,000–60,000, Polysciences, Inc.) was produced by co-dissolution of 0.6 and 1.8 gm of each polymer, respectively, in 20 cc of acetone at 52° C. The solution was transferred to molds and allowed to stand at room temperature. An acetone seal was applied to the gel after one hour to prevent surface drying at long demold times. The blended gel produced on demold after 21 hours was subsequently immersed in methanol for four days, 18 hours before drying at room temperature for one week. Shrinkage of the methanol-based material occurred on drying to the extent of 48%, to yield a practically solid polymer core. An acetone-based gel was immersed in methanol for five days, 18 hours, then immersed in water for 21 hours prior to drying. In this case, the microporous blend obtained exhibited a shrinkage of only 13% and a density of 0.25 gm/cm$^3$.

The density of microporous materials could be varied by water treatment subsequent to acetone extraction in methanol. Extraction of organic liquid from the material and its substitution by water removed the plasticizing effect of the organic molecules, raised the Tg and thereby restricted chain recoiling of the amorphous phase, which resulted in material shrinkage on drying.

25:75 acetone-based gels of L-PLA and 70:30 poly(DL-lactide co-glycolide) were demolded after 24 hours and immersed in methanol (50 cc methanol in 100 cc beaker) for three days, with a change of immersion medium at 24 hours. Samples were then air dried for time periods of 0, 60 and 80 minutes before immersion in water for three days, with a change in immersion medium at 24 hours. Samples were finally air dried under ambient conditions for three days to give uniformly microporous materials with the final shrinkage and density values shown in Table 1.

TABLE 1

| Air drying time (minutes) prior to water immersion | 0 | 60 | 80 |
|---|---|---|---|
| Final foam shrinkage (%) | 5 | 15 | 19 |
| Foam density (gm/cm$^3$) | 0.19 | 0.22 | 0.29 |

EXAMPLE 14

A 25:75 blended solution of L-PLA and 85:15 poly(DL-lactic co-glycolide) (MW 40,000–100,000, Dupont) was produced by dissolution of 0.8 gm and 2.4 gm of each polymer, respectively, in 20 cc acetone at 52° C. The solution was transferred to molds and allowed to stand at room temperature. A cloud point was observed after approximately 15 minutes. On demold after 24 hours, gel samples were air dried for time periods of 0, 15, 45, and 75 minutes before immersion in water for three days, with a change of immersion medium after 48 hours. Drying of the microporous materials resulted in the final shrinkage and density values shown in Table 2, with foam properties ranging from tough and pliable to hard-yet-tough as density increased with predry time.

TABLE 2

| Air drying time (minutes) prior to water immersion | 0 | 15 | 45 | 75 |
|---|---|---|---|---|
| Final foam shrinkage (%) | 8 | 10 | 17 | 20 |
| Foam density (gm/cm$^3$) | 0.22 | 0.25 | 0.32 | 0.38 |

EXAMPLE 15

Poly(DL-lactide) (MW 40,000–100,000, Dupont) was dissolved in acetone to produce a 12% (w/v) solution, transferred to a 10 cc syringe body and allowed to stand at room temperature. Gelation did not result and solvent evaporation occurred over seven days, to leave a coating on the mold walls. A 25:75 blended solution of L-PLA and poly(DL-lactide) was produced by co-dissolution of 0.8 gm and 2.4 gm of each polymer, respectively, in 20 cc acetone at 52° C. The solution was transferred to molds and allowed to stand at room temperature. A cloud point was observed after approximately 10 minutes. An acetone seal was applied to the gel after 30 minutes to prevent surface drying at long demold times. On demold after 21 hours, a soft gel was obtained, which was immersed in methanol for three days with a change of immersion medium after 22 hours. Immersion of the methanol-based material for three days in water, with a change in medium after 24 hours, prior to air drying resulted in a white, microporous material which exhibited a shrinkage of 1% and a density of 0.18 gm/cm$^3$.

On demold after 21 hours, an acetone-based gel sample was air dried for 65 minutes before immersion in water for three days, with a change of immersion medium after 24 hours. Drying of the microporous material so obtained resulted in a final shrinkage of 26% and a density of 0.40 gm/cm$^3$.

L-PLA can be used as a gelling medium to incorporate non-gelling polymers in a particular material composition for adjustment of resorption rates, for example.

EXAMPLE 16

A 50:50 blended solution of L-PLA and low molecular weight polycaprolactone (MW 15,000, Polysciences, Inc.) was prepared by co-dissolution of 0.7 gm of each polymer in 10 cc acetone at 52° C. The solution was transferred to a mold and allowed to stand at room temperature. A cloud point was observed after 30 minutes. A firm, white damage-tolerant gel was obtained on demold after 25 hours, which was immersed in methanol for two days, 21 hours. Drying of this methanol-based material at room temperature for two days, 19 hours resulted in a shrinkage of 30% and a density of 0.45 gm/cm$^3$ for the resulting firm, white, microporous material.

Treatment of the methanol-based material in a 50% methanol/water mixture for two days, 19 hours, then water for six days prior to air drying for four days resulted in a microporous material which exhibited a shrinkage of 15% relative to the demolded gel and a density of 0.25–0.29 l gm/cm$^3$. DSC revealed melting transitions at 64° C. and 160° C., corresponding to the individual blend components.

EXAMPLE 17

A 50:50 blended solution of L-PLA (MW 100,000 Polysciences, Inc.) and DL-lactide (MW 144.12, Polysciences, Inc.) was prepared by co-dissolution of 0.7 gm of each material in acetone at 52° C. the solution was transferred to a cylindrical mold and allowed to stand at room temperature. An acetone seal was applied after 30 minutes. A firm, white, damage-tolerant gel was obtained on demold after 24 hours, which was immersed in methanol for two days, 21 hours. Drying of this methanol-based material for two days, 19 hours resulted in a hard, white microporous material exhibiting a shrinkage of 37% relative to the demolded gel and a density of 0.38 gm/cm$^3$. Treatment of the methanol-based material for two days, 19 hours in a 50% methanol/water mixture, followed by immersion in water for six days, prior to air drying (four days), resulted in a firm, white microporous material which exhibited a shrinkage of 19% and a density of 0.6 gm/cm$^3$. DSC revealed a small melting peak at 60° C. and the main melting transition at 160° C.

EXAMPLE 18

A bone repair device potentially suitable for general bone augmentation and reconstruction or for repairing large segmental defects and nonunion fractures was fabricated from a microporous 25:75 blend of L-PLA and 85:15 poly(DL-lactide co-glycolide) produced by the disclosed gel casting technique.

0.6 gm of L-PLA (MW 100,000) and 1.8 gm of 85:15 poly(DL-lactide co-glycolide) copolymer (Medisorb, MW 40,000–100,000, Dupont) were dissolved with stirring in 20 cc acetone at 52° C. in approximately 15 minutes. The solution was transferred to molds and allowed to stand at room temperature for 24 hours before demold. The gel obtained was dried in air for 45 minutes to give a shrinkage of 19% then immersed in water for three days, with a change in immersion medium after 24 hours. Air drying of the microporous material obtained over four days resulted in a final shrinkage of 17% and a density of 0.32 gm/cm$^3$. This stock material was machined further to produce a particular honeycomb design for repair of long bones.

EXAMPLE 19

Fabrication of Implants: A 50%–50% copolymer (PLG50) of PLA and PGA (intrinsic viscosity 0.65 dL/g, MW 45,000 daltons, Medisorb Inc., Cincinnati, Ohio) was used to fabricate the specimens. A 15% (w/v) solution of PLG50 was prepared in HPLC grade acetone under continuous stirring and low heat (40° C). This solution was poured into a specially designed Teflon® mold having piano wires spaced corresponding to the holes shown in FIG. 2 and a central channel corresponding to the central hole shown in FIG. 2. The mold was then capped and allowed to stand at room temperature until the solution formed a gel. A small amount of acetone was added to the top of the gel to prevent it from drying. After 24 hours the gel was extracted from the mold and processed through several stages of solvent exchange as follows: immersion for 24 hours in methanol:acetone 1:2 (v/v), followed by soaking in 1:1 and 2:1 (v/v) methanol:acetone mixtures for 24 hours each. During this process the implant precipitated as a microporous solid with pores approximately 5 to 20 μm in size. The resulting disc-shaped implant as shown in FIGS. 1 and 2 was 13.5 mm in diameter, 2.5 mm in thickness and weighed approximately 150 mg.

Protein (15 mg/implant) was incorporated into the implant prior to gel formation. BMP was purified from canine bone using a modification of the method of Urist et al. ("Purification of bovine Bone Morphogenetic Protein by Hydroxyapatite Chromatography", Natl. Acad. Sci. (1984) 81:371–375) as described previously (Heckman, J. D. et al., "The Use of Bone Morphogenetic Protein in the Treatment of Non-Union in a Canine Model," J. Bone and Joint Surg. (1991) 73-A:750–764). When BMP is isolated in this manner it is hydrophobic and dissolves in organic solvents like acetone or chloroform. Due to the low availability of recombinant BMP and the high cost of purified growth factors, we also examined release kinetics of a model protein, soybean trypsin inhibitor (TI). TI was selected because of its hydrophobic character, the fact that it has a molecular weight comparable to that of BMP, and its availability (Sigma chemical Company, St. Louis, Mo.). TI was used for the studies described below; a small number of implants were also fabricated with purified canine BMP.

The amount of protein actually retained in the implant following the fabrication process was determined. The utensils, glassware and mold used for fabrication were washed with ultrapure distilled water. The washes were retained for measurement of protein content using the micro BCA method. The results indicated that approximately 80 percent of the protein added to the implant was lost during fabrication.

Activity of BMP in the implant was verified as the ability of the implant to induce bone formation when placed in the thigh muscle of nude mice. Representative implants made with each batch of BMP were implanted as described by Heckman et al. ("The Use of Bone Morphogenetic Protein in the Treatment of Non-Union in a Canine Model," J. Bone and Joint Surg. (1991) 73-A:750–764). After 28 days, the tissue was excised and examined by routine histology. All implants containing BMP supported bone formation, whereas those without BMP did not. TI implants were not tested in this manner.

EXAMPLE 20

Protein Release Kinetics: A total of 48 test specimens were fabricated with TI, weighed and then randomly divided into eight groups of six specimens each. These groups were subjected to hydrolytic degradation in phosphate buffered saline (PBS), pH 7.4, at 37° C. for test periods of 0, 2, 22, 32, 42, 52, 62, and 72 days respectively. Another 12 implants were fabricated without any TI. These were divided into two control groups of six specimens each and subjected to hydrolytic degradation in PBS for 0 and 72 days respectively. A separate group of six implants was fabricated with 15 mg of BMP each and was analyzed for a total of 20 days. Each specimen was immersed in 15 ml of PBS. For the first 48 hours 1.5 ml of PBS were removed several times a day and stored at −20° C. for later analysis. After this initial period, 1.5 ml of PBS were sampled every 48 hours after vortexing. After sampling the PBS in the tubes was replaced with fresh PBS in order to prevent a decrease in pH and thus simulate physiologic buffering.

Figure 5:
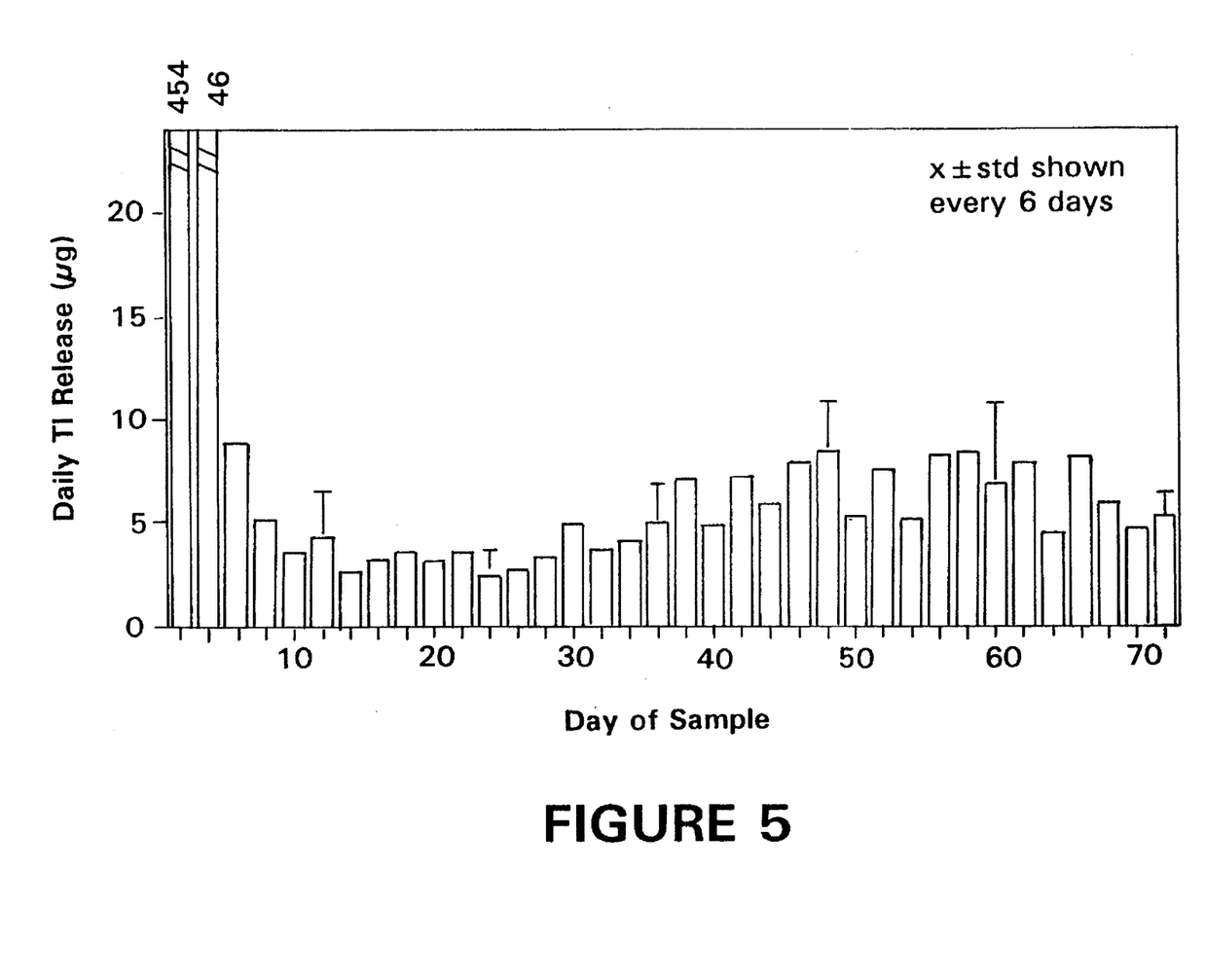
FIG. 5 graphs daily protein elution characteristics for implants as in FIG. 3 containing TI.
Figure 6:
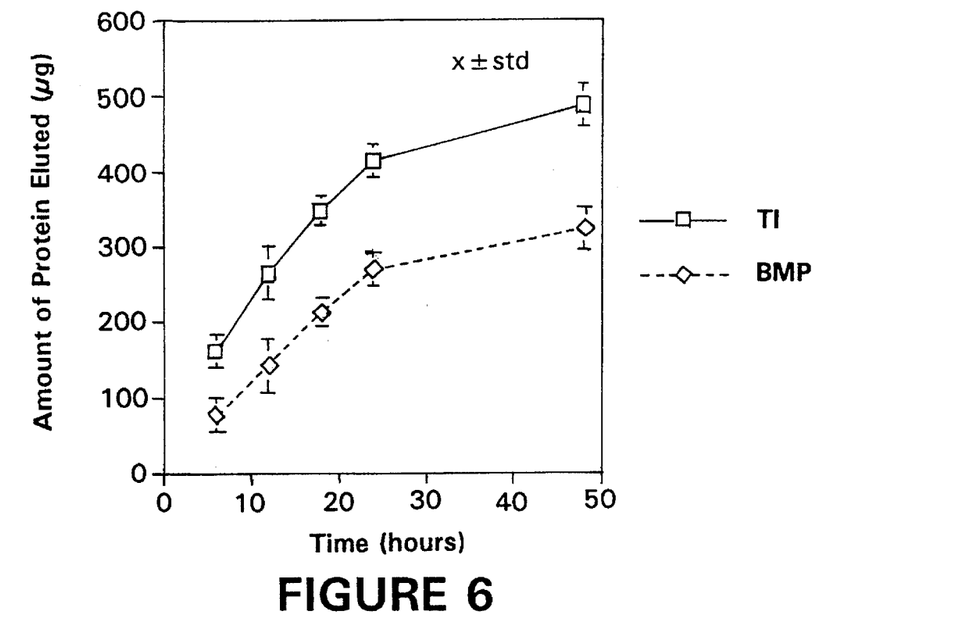
FIG. 6 graphs protein release characteristics for implants as in FIG. 3 containing TI and for implants as in FIG. 3 containing bone morphogenic protein (BMP) for the initial 48-hour period.
Figure 7:
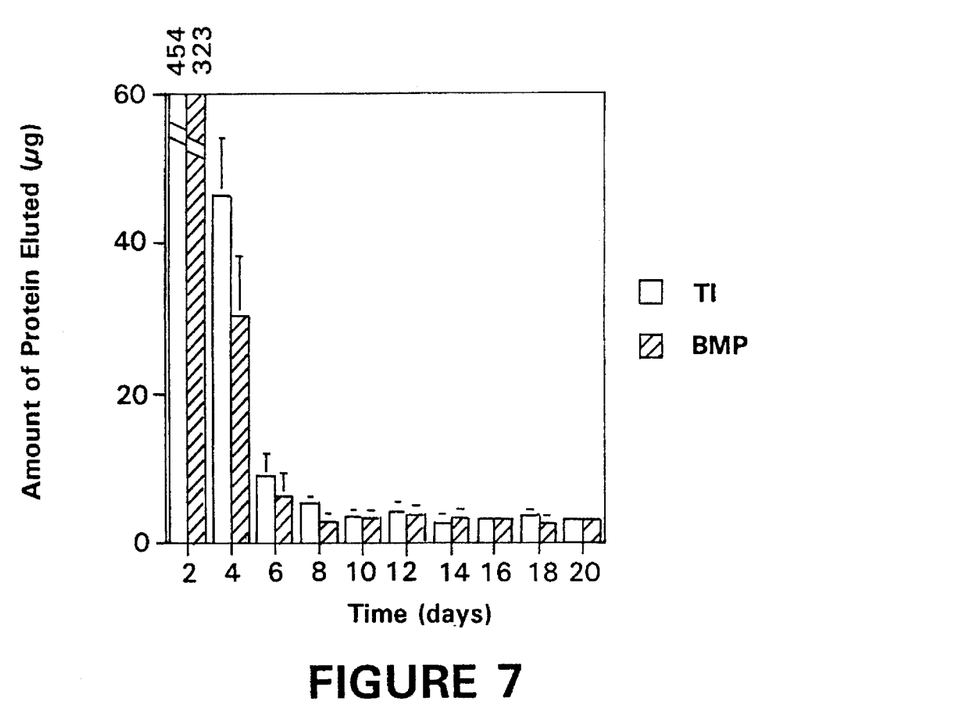
FIG. 7 graphs protein release patterns for implants as in FIG. 3 containing TI and BMP for a 20-day period.
Figure 8:
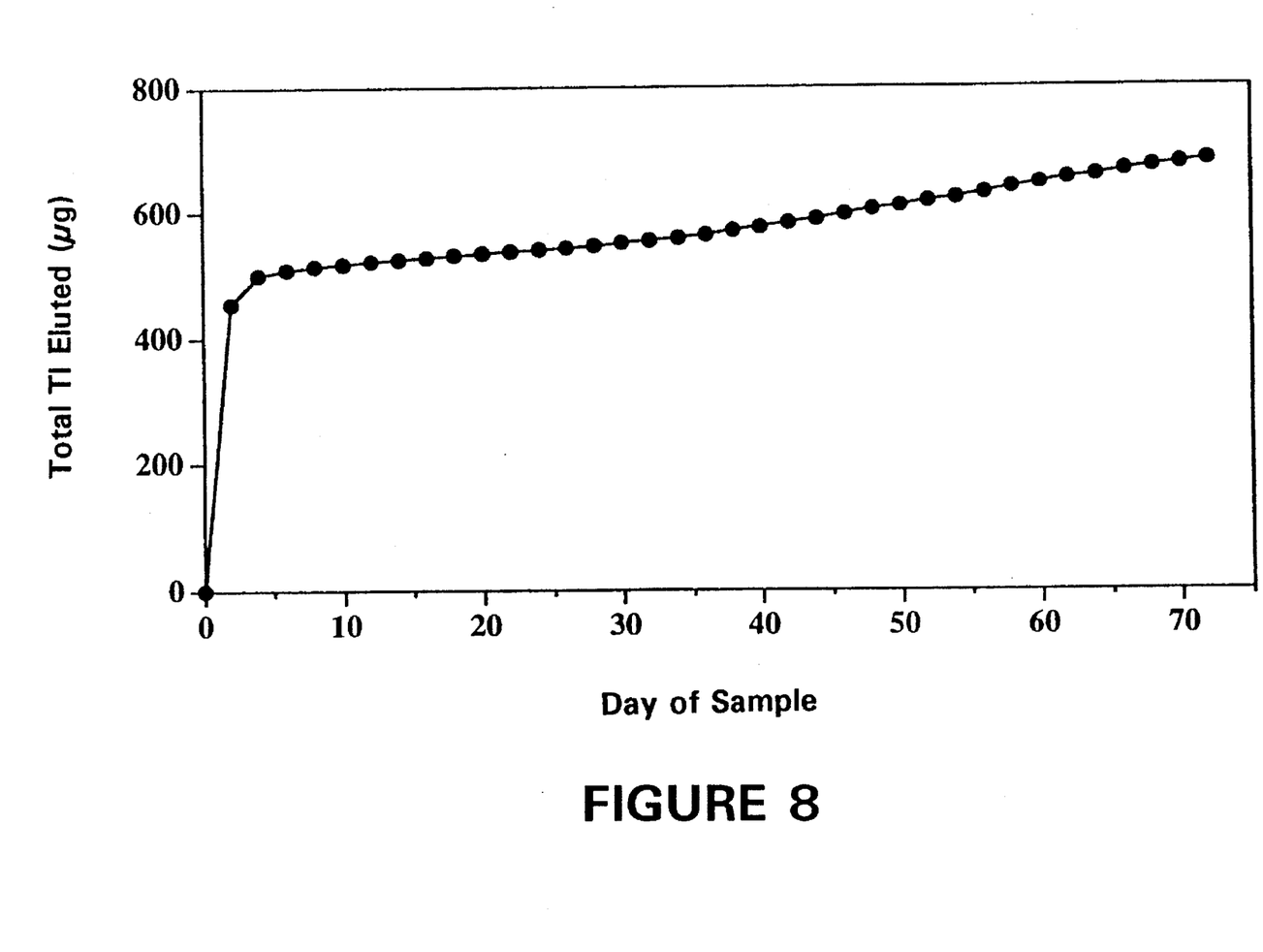
FIG. 8 shows cumulative protein elution as a function of time for 72 days for implants as in FIG. 3 containing TI.

A large fraction (66%) of TI in the specimens was eluted in the first 48 hours (FIG. 5). The elution rate was the lowest between 12 and 24 days, and then increased marginally. The BMP release in the first 48 hours followed a pattern similar to that of TI although the amount released was less (FIG. 6). BMP specimens released an average of 322 μg protein in the initial two days. Significant portions of this amount were released in the first 24 hours (FIG. 6). A comparison of BMP and TI elution over a period of 20 days again exhibited similar release patterns (FIG. 7), even though the amount of TI released in the first four days was higher than BMP. The cumulative protein loss from the TI specimens during the test period is shown in FIG. 8. These specimens released approximately 680 μg of TI over a test period of 72 days post-immersion.

The elution of BMP and TI from the biodegradable implants exhibited similar trends even though the amounts released in the first four days were significantly different in magnitude. After day 6 the differences in elution rate of the two proteins were only marginal. Thus, TI appears to be a reasonable model to predict the elution characteristics of BMP from the present biodegradable implant.

TI and BMP release from the implants included an initial burst during the first 48 hours. Since the specimens did not experience any significant loss in mass or molecular weight during this time period, it can be deduced that the protein release during this period is primarily diffusion controlled and not due to degradation of the implant. It is possible that the majority of the protein in this initial "burst release" comes from the surface of the specimen which subsequently becomes depleted of protein.

The later phase of increased protein release beginning at approximately 24 days was accompanied by significant decreases in both the molecular weight and mass of the specimens indicating rapid breakdown of the polymer due to hydrolysis. The release of TI from the test specimens in the present study appears to be two phased in nature: the first phase is diffusion controlled and is dominant at the beginning of the degradation process. The second phase is more dependent on degradation of the polymer and the protein release occurs in concert with polymer breakdown.

The present implant provides an initial burst of protein which serves to augment the in vivo wound healing response. As mesenchymal cells migrate to the wound site and undergo differentiation, the second stage release provides continued exposure to differentiation factors. Many growth factors act on cells at different points in their differentiation and maturation with varying effects. For example, a factor may be mitogenic for undifferentiated mesenchymal cells, promoting their proliferation at the wound site. Following the proliferative phase, the growth factor may promote differentiation of a chondrogenic or osteogenic phenotype.

This is particularly important in prevention and treatment of nonunions, where it is often necessary for undifferentiated cells to migrate long distances and to proliferate and differentiate in hypovascularized regions. Studies examining healing of critical size craniotomy defects, suggest that lack of an adequate supply of needed factors may contribute to fibrocartilage development typical of nonunions (Schmitz, J. D. et al. (1990) "Characterization of Rat Calvarial Nonunion Defects," Acta Anatomica, pp 185–192). In the reported model, this occurred approximately 17–20 days after creation of the critical size defect, about the same time that the second phase of protein release was seen in the in vitro assays reported here.

EXAMPLE 21

Polymer Degradation: At the end of each test period described above the specimens were removed from PBS, vacuum dried for 72 hours and massed on an electronic balance. The polymer was analyzed for molecular weight using gel permeation chromatography with chloroform as the mobile phase and polystyrene standards (Aldrich, Milwaukee, Wis.). The amount of TI or BMP released was measured as a function of protein content using a micro BCA assay (Pierce, Rockford, Ill.; Lot No. 931112150). A Student's t-test was performed to detect significant differences.

Figure 3:
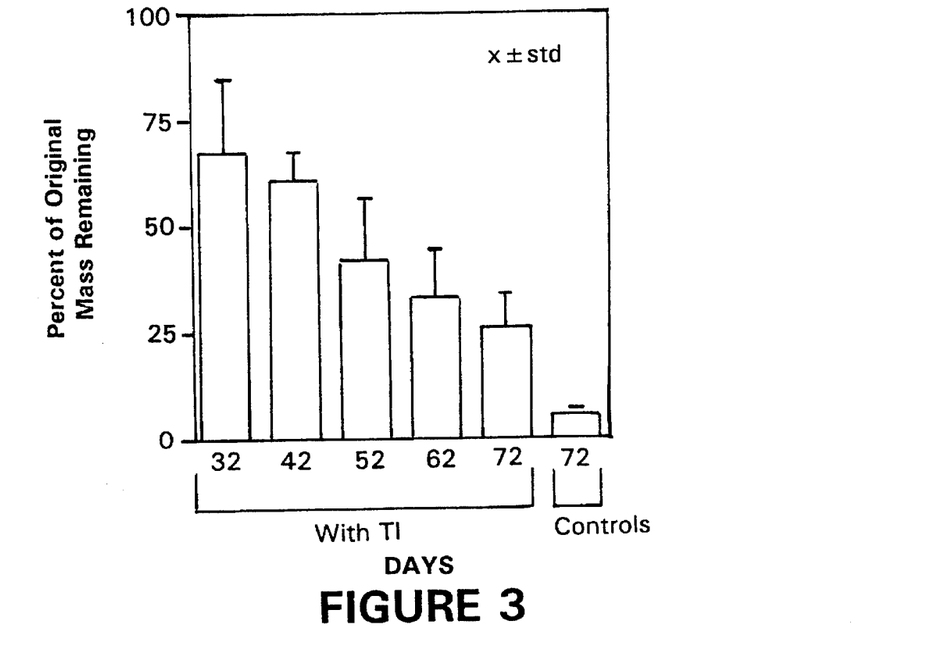
FIG. 3 graphs loss of mass as a function of degradation time for biodegradable implants of this invention for fracture nonunions fabricated from a 50:50 copolymer of (D,L) polylactic acid-polyglycolic acid (PLA:PGA) having a diameter of 13.5 mm and a thickness of 2.5 mm. The implants contain soybean trypsin inhibitor (TI). TI-containing implants are compared with controls without TI at 72 days.

All the specimens subjected to hydrolytic degradation in PBS exhibited a decrease in mass and molecular weight as a function of time. The test specimens with TI lost approximately 33% of their mass in the first 32 days (FIG. 3). Mass loss increased in a steady fashion thereafter and reached 74% in 72 days. However, the control group with no protein content lost approximately 90% of its mass during the same period.

Figure 4:
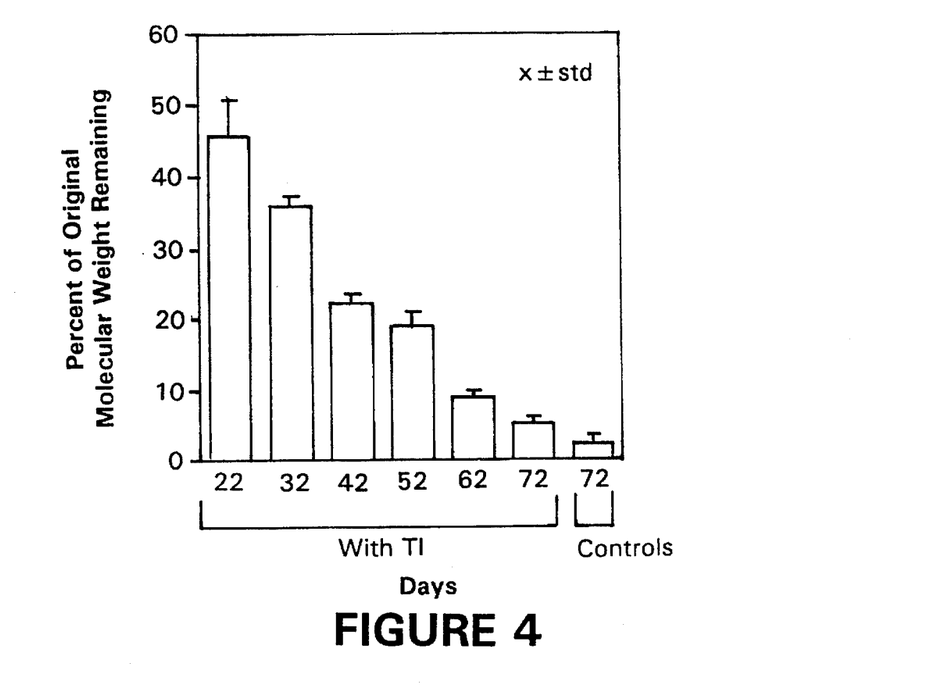
FIG. 4 graphs loss of weight (average molecular weight) as a function of degradation time for implants as in FIG. 3. The implants contain TI. TI-containing implants are compared with controls without TI at 72 days.

Compared to the mass, the molecular weight (weight average) of the protein specimens decreased 65% in the first 32 days and 94% in 72 days (FIG. 4). At the end of 72 days the control specimens had suffered a 97% loss in their molecular weight.

The implants underwent degradation under the experimental conditions used, whether or not protein was incorporated into the polymer. The starting weight average molecular weight of the polymer was approximately 45,000 daltons. In 72 days it decreased to approximately 2,700 daltons for the test implants with TI and to 910 daltons in the absence of TI. At this time only small portions of these implants remained, which were gel-like and sticky in nature, indicative of low molecular weight.

The loss in the molecular weight of the implants exhibited a more rapid decrease than the corresponding mass loss. This behavior is typical of the degradation characteristics of PLA-PGA polymers. Hydrolytic scission of the molecular chains of these polymers starts upon contact with water. However, the initial degradation products are too large to freely diffuse from the bulk implant and as a result the mass loss is minimal. After a period of time, as degradation continues, the molecular chains are sufficiently reduced in size to exit the bulk and cause a significant decrease in mass. For example Schankenraad et al. ("Enzymatic activity toward poly(L-lactic acid) implants," J. Biomed. Mat. Res. (1990) 24:529–545) have reported that for L-PLA there is an exponential decrease in mass once the molecular weight decreases below 5,000 daltons.

The presence of protein affected both loss of molecular weight and loss of mass. After a degradation period of 72 days the specimens with the protein lost approximately 95 percent of their molecular weight compared to a 98 percent loss for the control specimens with no protein. This statistically significant difference ($p<0.05$) was even more pronounced for the case of mass loss (FIG. 5). These results suggest that the presence of TI in the specimen decreases the degradation rate of the polymer.

The degree and nature of micropores may have contributed to this effect of protein on polymer degradation. Implants with proteins exhibited a more evenly distributed porosity with small pores with an approximate size of 20 μm. On the other hand, the control specimens exhibited larger (60 μm) but fewer number of pores. It is possible that the pores in the protein specimens were caused by dissolution of protein aggregates during the fabrication process. A greater number of pores would usually imply a larger surface area exposed to water and hence a faster rate of degradation. However, the results of this study indicate a higher rate of degradation for implants with the lower porosity implying that factors other than porosity may be dominant.

The crystallinity of the implant polymer can play a significant role in determining its rate of degradation. According to Gilding and Reed, copolymers of DL-PLA and PGA are predominantly amorphous when the PGA content is more than 30 percent. However, as reported in Coombes, A. G. A. and Heckman, J. D. (1992) "Gel casting of resorbable polymers 1. Processing and applications." Biomaterials 13:217–224; and Coombes, A. G. A and Heckman, J. D. (1992) "Gel casting of resorbable polymers 2. In vitro degradation of bone graft substitutes," Biomaterials 13:297–307, both gel cast and as-received PLG50 exhibit several small melting peaks on a thermogram. Such melting points are indicative of some degree of crystallization and are signs of crystallization of chain segments of the copolymer (Murdoch, J. R. and Loomis, G. L., "Polylactide Compositions," U.S. Pat. No. 4,719,246 1988). Coombes, A. G. A. and Heckman, J. D. (1992) "Gel casting of resorbable polymers 1. Processing and applications.," Biomaterials 13:217–224 suggest that acetone based gels of PLG50 similar to those used in the present study are formed due to "effective entanglements" and small quantities of lamellar crystals which serve as anchor points for the 3-dimensional network of polymeric chains.

In the present study it was observed that specimens containing a protein gelled in approximately 3 to 4 hours, while the control specimens (without any proteins) took approximately 5 to 6 hours to form a stable gel. It is possible that the protein molecules aid in the formation of the 3-dimensional network that is necessary for gel formation. The proteins may either act as tie molecules and provide "effective entanglements" between anchor points of the gel, or they may serve as "seeds" for polymer crystallization and possibly increase the number of crystalline sites. Such an increase would then be reflected in a slower rate of degradation. Alternatively it is possible that TI binds to the polymer by some complex mechanism and hinders its hydrolysis.

EXAMPLE 22

Implant Morphology: Representative control specimens as well as specimens with TI and BMP were subjected to cryogenic fracture at liquid nitrogen temperatures to obtain surfaces free of deformation for microstructural studies. These specimens had not been subjected to degradation in PBS. The exposed cross-sectional fracture surfaces were sputter coated with gold-palladium and examined in a scanning electron microscope.

The scanning electron microscopy showed that the specimens with BMP and TI were microporous in nature with an even distribution of similar sized pores. No differences as a function of protein used were observed. The control specimens on the other hand did not reveal the same degree of even porosity.

EXAMPLE 23

A 100,000 molecular weight poly(L-lactide) obtained from Polysciences, Inc. (Batch No. 61490) was supplied in a fine, string or fibrous precipitate form and dissolved readily in acetone at 52° C. Poly(L-lactide) polymer obtained from Dupont [Batch No. 59010 L051, weight average molecular weight (MW)-100,000] was supplied in the form of solid platelets or pellets (approximately 4×15×1 mm), which were presumably produced by melt extrusion. Dissolution of the pellets was not achieved in acetone (0.4 gm in 10 cc solvent) at 52° C. in one hour and they retained their starting form without coalescing. In contrast, the Dupont material in precipitate form dissolved readily in acetone at 52° C. to produce a 4% (w/v) solution. Gelation occurred on standing at room temperature in less than 15 minutes. The poly(L-lactide) precipitate can be prepared, for example, by dissolution of 2 gm of polymer in 20 cc methylene chloride at room temperature, followed by precipitation in 40 cc methanol which is agitated by a stirrer bar. The precipitate is dried at room temperature before use.

Dissolution of the above-mentioned Dupont poly(L-lactide) in acetone was also facilitated by using the film form of the polymer. As-received pellets were converted to a film by casting a 10% (w/v) solution of the polymer in methylene chloride on a glass surface, followed by drying.

The instant invention has been disclosed in connection with specific embodiments. However, it will be apparent to those skilled in the art that variations from the illustrated embodiments may be undertaken without departing the spirit and scope of the invention.

We claim:

1. An implant for placement in nonunion bone fractures comprising:
   a. interconnected pores having an average diameter of between about 5 μm and about 20 μm constituting a void volume of between about 40 and about 85 percent of said implant;
   b. canals having a size, shape and spacing substantially corresponding to Haversian canals;
   c. having a thickness of between about 1 mm and about 15% of the length of the bone;
   d. having a perimeter shaped to substantially correspond to the cross-section of the ends of said nonunion bone fracture;
   e. having a carvable, non-friable consistency.

2. The implant of claim 1 composed of a bioerodible polymer.

3. The implant of claim 2 composed of a bioerodible polymer comprising PLA.

4. The implant of claim 3 composed of a bioerodible polymer comprising a copolymer of PLA and PGA.

5. The implant of claim 1 having a substantially circular perimeter.

6. The implant of claim 1 also comprising a central channel therethrough having a diameter of between about 7 and about 35 mm.

7. The implant of claim 1 further comprising an additive selected from the group consisting of therapeutically active substances, degradation enhancers, degradation retardants, antibiotics, growth hormones, enzymes, immune modulators, vaccines, and medicaments.

8. The implant of claim 1 also comprising BMP.

9. The implant of claim 7 further comprising a degradation retardant which is a non-immunogenic protein having a molecular weight at least about 15,000.

10. The implant of claim 1 produced by a polymer gel casting method.

11. The implant of claim 10 comprising a PLA:PGA copolymer having a molecular weight of between about 45,000 and about 200,000.

12. The implant of claim 10 formed by a process comprising:
    a. solubilizing said polymer in an organic solvent to form a solution;
    b. allowing said solution to gel in a mold to form said implant;
    c. removing said gel from said mold;
    d. removing said organic solvent from said gel.

13. The implant of claim 12 made by a process wherein said organic solvent is removed from said gel by means of solvent extraction.

14. The implant of claim 7 designed to release between about half and about two-thirds of said additive within the first two days of implantation in vivo and thereafter to continuously release a substantially constant amount of said additive over the degradation period of said implant.

15. A method for treating a nonunion bone fracture comprising placing into said fracture an implant comprising:
    a. interconnected pores having an average diameter of between about 5 μm and about 20 μm constituting a void volume of between about 40 and about 85 percent of said implant;
    b. canals having a size, shape and spacing substantially corresponding to Haversian canals;
    c. having a thickness of between about 1 mm and about 15% of the length of the bone;
    d. having a perimeter shaped to substantially correspond to the cross-section of the ends of said nonunion bone fracture;
    e. having a carvable, non-friable consistency.

16. A method of making an implant for treating a nonunion bone fracture comprising:
    a. solubilizing a biodegradable polymer precursor in an organic solvent to form a solution;
    b. allowing said solution to gel in a mold comprising tines spaced to form canals in said implant having a size, shape and spacing substantially corresponding to Haversian canals;
    c. removing said gel from said mold;
    d. removing said organic solvent from said gel by solvent extraction whereby said polymer precipitates as a microporous solid implant having pores about 5 to about 20 μm and forming a void volume between about 40 and about 85 percent of said implant.

17. The method of claim 16 also comprising adding an additive selected from the group consisting of therapeutically active substances, degradation enhancers, degradation retardants, antibiotics, and growth hormones to said solution of step a. prior to allowing said solution to gel.

18. The method of claim 17 comprising rotating said mold during step b. whereby said active substance remains evenly distributed throughout said solution during gel formation.

* * * * *